United States Patent [19]

Meyers

[11] Patent Number: 5,531,119

[45] Date of Patent: Jul. 2, 1996

[54] ULTRASOUND PROBE WITH BUBBLE TRAP

[75] Inventor: Paul F. Meyers, San Juan Capistrano, Calif.

[73] Assignee: Capistrano Labs, Inc., San Clement, Calif.

[21] Appl. No.: 230,160

[22] Filed: Apr. 19, 1994

[51] Int. Cl.[6] .............................. A61B 8/00; G01H 17/00
[52] U.S. Cl. ......................... 73/661; 73/644; 128/660.01; 367/140; 367/171
[58] Field of Search ............... 73/661, 644; 128/660.01; 367/140, 171, 172

[56] References Cited

U.S. PATENT DOCUMENTS

| | | | |
|---|---|---|---|
| 3,955,561 | 5/1976 | Eggleton | 128/2.052 |
| 4,092,867 | 6/1978 | Matzuk | 73/609 |
| 4,106,346 | 8/1978 | Matzuk | 73/614 |
| 4,149,419 | 4/1979 | Connell, Jr. et al. | 73/621 |
| 4,246,792 | 1/1981 | Matzuk | 73/620 |
| 4,271,706 | 6/1981 | Ledley | 73/614 |
| 4,282,879 | 8/1981 | Kunii et al. | 128/660 |
| 4,316,271 | 2/1982 | Evert | 367/140 |
| 4,341,120 | 7/1982 | Anderson | 73/618 |
| 4,375,818 | 3/1983 | Suwaki et al. | 128/660 |
| 4,391,282 | 7/1983 | Ando et al. | 128/660 |
| 4,398,425 | 8/1983 | Matzuk | 73/633 |
| 4,399,703 | 8/1983 | Matzuk | 73/621 |
| 4,401,123 | 8/1983 | Baba | 128/660 |
| 4,421,118 | 12/1983 | Dow et al. | 128/660 |
| 4,424,813 | 1/1984 | Havlice et al. | 128/660 |
| 4,466,443 | 8/1984 | Utsugi | 128/660 |
| 4,474,184 | 10/1984 | Harui | 128/660 |
| 4,479,388 | 10/1984 | Matzuk | 73/634 |
| 4,483,326 | 11/1984 | Yamaka et al. | 128/4 |
| 4,545,117 | 10/1985 | Okamoto | 29/596 |
| 4,584,880 | 4/1986 | Matzuk | 73/609 |
| 4,646,722 | 3/1987 | Silverstein et al. | 128/4 |
| 4,674,515 | 6/1987 | Andou et al. | 128/660 |
| 4,675,563 | 6/1987 | Goldowsky | 310/15 |
| 4,722,345 | 2/1988 | Ueno et al. | 128/660 |
| 4,756,313 | 7/1988 | Terwilliger | 128/660 |
| 4,785,819 | 11/1988 | Pearce | 128/660.10 |
| 4,807,634 | 2/1989 | Enjoji et al. | 128/660.01 |
| 4,831,292 | 5/1989 | Berry | 310/15 |
| 4,841,979 | 6/1989 | Dow et al. | 128/660.10 |
| 4,850,362 | 7/1989 | Rello et al. | 128/660.05 |
| 4,893,628 | 1/1990 | Angelsen | 128/660.05 |
| 4,913,155 | 4/1990 | Dow et al. | 128/660.1 |
| 4,930,515 | 6/1990 | Terwilliger | 128/662.06 |
| 5,012,147 | 4/1991 | Bertram et al. | 310/80 |
| 5,048,529 | 9/1991 | Blumenthal | 128/660.1 |
| 5,085,221 | 2/1992 | Ingebrigtsen et al. | 128/660.1 |
| 5,088,495 | 2/1992 | Miyagawa | 128/660.1 |
| 5,111,092 | 5/1992 | Reinicke | 310/688 |

Primary Examiner—Hezron E. Williams
Assistant Examiner—Richard A. Moller
Attorney, Agent, or Firm—Stetina Brunda & Buyan

[57] ABSTRACT

An ultrasound probe housing has at least one air bubble trap disposed therein and configured to facilitate movement of air bubbles away from a window thereof and also configured to resist movement of the air bubbles back toward the window. Preferably, two air bubble traps are utilized, one proximate the ultrasound transducer and the other proximate the motor thereof, so as to facilitate isolation of the ultrasound transducer and motor from air bubbles. The air bubble traps are preferably configured as funnels having a narrow end thereof oriented away from the window and having a wide end thereof oriented toward the window such that air bubbles easily enter the wide end thereof but do not easily enter the narrow end thereof. The air bubbles preferably move to a fluid expansion compensation chamber wherein they become captured and provide compensation for thermal expansion of the ultrasound transmissive fluid contained within the ultrasound probe.

5 Claims, 2 Drawing Sheets

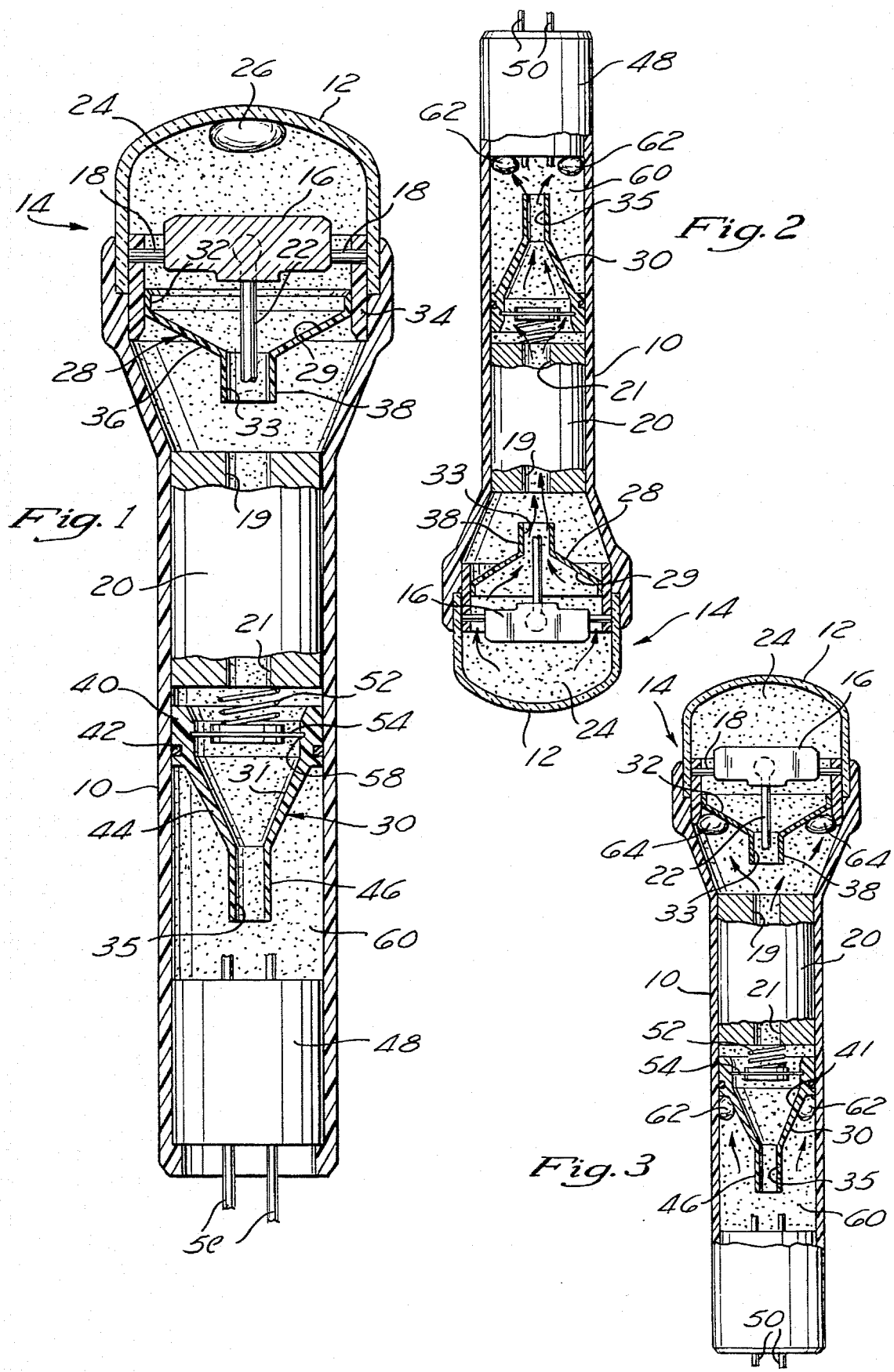

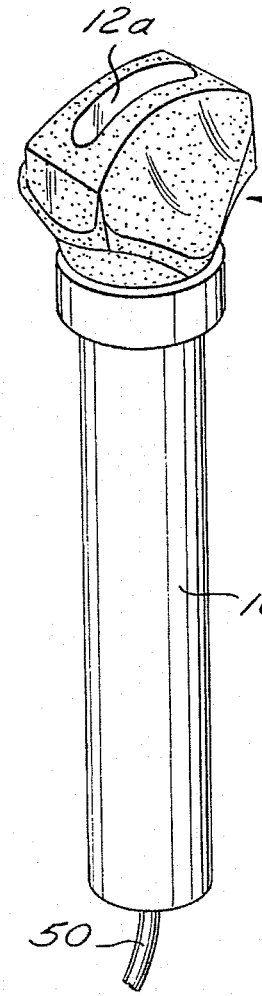
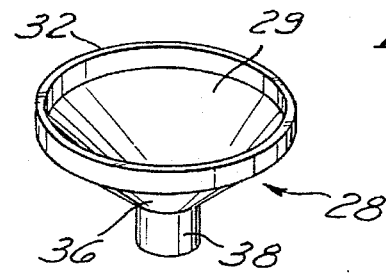
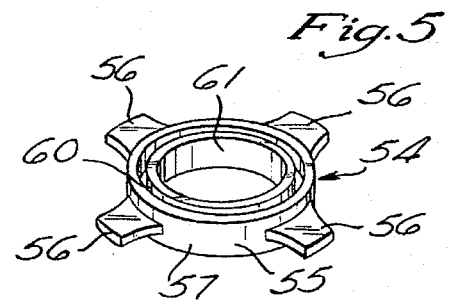
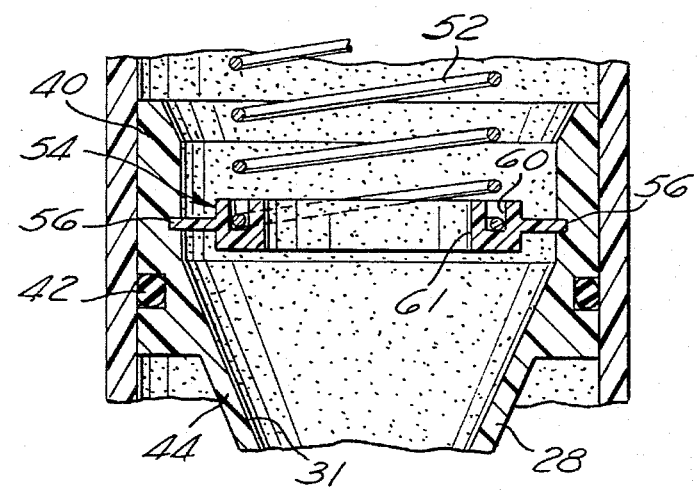
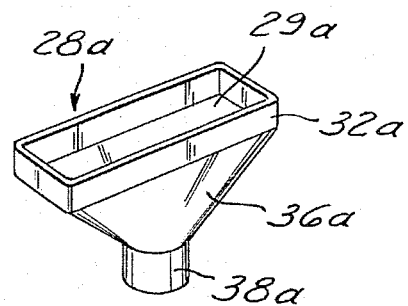

ULTRASOUND PROBE WITH BUBBLE TRAP

FIELD OF THE INVENTION

The present invention relates generally to ultrasound probes such as those commonly used for real-time ultrasound diagnostic and therapeutic procedures, and more particularly to an ultrasound probe having at least one air bubble trap which prevents the accumulation of air bubbles proximate the window thereof which interfere with the radiation of ultrasound energy from the ultrasound probe's transducer.

BACKGROUND OF THE INVENTION

In the field of ultrasound diagnostics, acoustic images of body tissue are obtained. In order to produce real-time images, beams of ultrasound energy from an ultrasound probe are transmitted into the body tissue of a patient and echoes received by the ultrasound probe are rapidly processed to provide an image format suitable for display. Desirably, the probe will produce an image over a wide field of view using a sector scan format. A sector scan image is produced by repeatedly transmitting and receiving ultrasound energy in radial directions from the probe. The ultrasound beam is directed by a mechanically moving transducer which is physically swept about a pivot axis through an arc to produce a sector scan.

The prior art is replete with examples of ultrasound transducer probe assemblies, such as those disclosed in U.S. Pat. No. 4,149,419 entitled "Ultrasound Transducer Probe" issued Apr. 17, 1979 to R. Connell et al; U.S. Pat. No. 3,955,561 entitled "Cardioscan Probe" issued May 17, 1976 to R. Eggleton; U.S. Pat. No. 4,421,118 entitled "Ultrasound Transducer" issued Dec. 20, 1983 to J. Dow et al; U.S. Pat. No. 4,479,388 entitled "Ultrasound Transducer and Rive System" issued on Oct. 30, 1984 to T. Matzuk; U.S. Pat. No. 4,399,703 entitled "Ultrasound Transducer and Integral Drive Circuit Therefor" issued on Aug. 23, 1983 to T. Matzuk; U.S. Pat. No. 4,092,867 entitled "Ultrasound Scanning Apparatus" issued on Jun. 5, 1978 to T. Matzuk; U.S. Pat. No. 4,246,792 entitled "Self-Contained Ultrasound Scanner" issued Jan. 27, 1981 to T. Matzuk; and U.S. Pat. No. 4,398,425 entitled "Ultrasound Scanning Transducer" issued on Aug. 16, 1983 to T. Matzuk.

Such ultrasound probes commonly utilized an ultrasound transducer disposed within the probe head and oriented so as to radiate ultrasound energy from the probe head through a window formed therein. The probe head, and typically a portion of the body or housing of the ultrasound probe as well, is filled with an ultrasound transmissive fluid, typically an oil.

One long-standing problem commonly associated with such contemporary ultrasound probes is the formation of air bubbles within the ultrasound transmissive fluid. Such air bubbles, when disposed between the ultrasound transducer and the window, interfere with the radiation of ultrasound energy from the transducer into the patient, thereby degrading the performance of the ultrasound probe.

It is similarly undesirable to allow air bubbles to remain proximate the motor of an ultrasound probe. Such motors typically rely upon conduction provided by the ultrasound transmissive fluid to provide heat dissipation therefore. As such, air bubbles proximate the motor interfere with heat dissipation and may consequently result in substantial damage to the motor. Air bubbles may also potentially vary the electrical or dynamic characteristics of the motor in an undesirable manner. As such, according to contemporary methodology, it is desirable to eliminate or remove bubbles from the probe.

Visible air bubbles typically form within ultrasound probes when smaller, often invisible, air bubbles unite to form larger air bubbles, and as components of the ultrasound probe out gas various vapors. Additionally, various gasses dissolved within the ultrasound transmissive fluid are believed to accumulate as well.

As used herein, the term air bubbles refers to any gaseous bubbles formed within the ultrasound probe. Such air bubbles do not necessarily contain the well known components of air, e.g., nitrogen, oxygen, carbon dioxide, etc. Rather, as those skilled in the art will appreciate, such air bubbles may contain oil vapors, solvent vapors, and a wide variety of other gaseous components.

According to contemporary practice, such air bubbles are typically removed by technicians, typically at a maintenance facility. The air bubbles are frequently removed by draining and replacing the ultrasound transmissive fluid. However, the air bubbles may be removed by merely adding fluid to the ultrasound probe (topping off).

Filling of the ultrasound probe with oil is preferably accomplished under vacuum so as to prevent the undesirable introduction of gasses which may form bubbles therein.

Some manufactures provide a vent/fill hole in the housing of the ultrasound probe to facilitate the use of a syringe to remove bubbles therefrom and to facilitate the addition of oil thereto.

It is generally not desirable to have bubbles removed by the user, typically either a medical doctor or an ultrasound technician. The removal of bubbles from an ultrasound probe inherently requires that additional ultrasound transmissive fluid be added to the ultrasound probe to compensate for the volume of air removed therefrom. When such fluid is added by untrained personnel, the ultrasound probe is frequently filled with an undesirable fluid, thereby degrading the performance thereof and/or damaging the ultrasound probe. Frequently, the wrong type of oil is used to fill or top off the ultrasound probe. It has even been known for inexperienced personnel to add water to ultrasound probes, resulting in corrosion to the interior components thereof.

All prior art efforts to date have been focused upon removing air bubbles from the ultrasound probe so as to eliminate the well-recognized problems associated therewith. As discussed above and well-recognized by those skilled in the art, the removal of air bubbles from ultrasound probes presents inherent problems itself.

Although the prior art has repeatedly attempted to solve the problem of air bubbles disposed within the ultrasound probe housing, such repeated attempts have heretofore been ineffective since continued outgassing, leakage, etc., constantly replenishes the air bubbles. Thus, any attempt to remove air bubbles from the ultrasound probe is only temporarily effective since such air bubbles inevitably reform.

Further, thermal expansion of the ultrasound transmissive fluid is typically compensated for in contemporary ultrasound probes via a bellows which facilitate changes in the fluid filled internal volume of the ultrasound probe in response to temperature changes of fluid. However, not only are such bellows expensive, but they are also subject to leakage. As such, it is desirable to provide a means for eliminating the requirement for such bellows-type fluid expansion compensation means.

SUMMARY OF THE INVENTION

The present invention takes a radical approach to solving the problem of air bubbles within ultrasound probes by recognizing that problems only occur when such air bubbles are located within specific portions of the ultrasound probe. Specific structures are provided within the housing to route and accumulate air bubbles in areas of the probe away from the window and motor to avoid the problems associated with such air bubbles in the prior art and also to allow the air bubbles to function as a thermal fluid expansion compensator.

The present invention thus addresses and alleviates the above mentioned deficiencies associated with the prior art. More particularly, the present invention comprises an ultrasound probe having a housing, an ultrasound transmissive window formed in the housing, and at least one air bubble trap disposed within the housing and configured to facilitate movement of an air bubble away from the window and also configured to resist movement of an air bubble toward the window. The air bubble traps are preferably configured as funnels having a narrow end thereof oriented away from the window and having a wide end thereof oriented toward the window. A tapered portion extends intermediate the wide end and the narrow end such a funnel is defined. Thus, contrary to prior art methodology, the present invention repositions air bubbles within the ultrasound probe housing, rather than attempting to remove the air bubbles therefrom.

Preferably, a first air bubble trap is disposed proximate the window for preventing the accumulation of air bubbles proximate the window and a second air bubble trap is disposed proximate the motor which facilitates oscillation of the ultrasound transducer. The second air bubble trap thus prevents air bubble accumulation proximate the motor. Thus, the first air bubble trap isolates the window from air bubbles and the second air trap isolates the motor from air bubbles.

It is desirable to isolate the motor from air bubbles since the motors commonly used in such ultrasound probes are cooled by conduction of heat away therefrom via the ultrasound transmissive fluid. Thus, air bubbles interfere with the heat dissipation process and may result in overheating of the motor and potential damage thereto.

Thus, the present invention recognizes that air bubbles located at positions other than intermediate the ultrasound transducer and window or approximate the motor are generally not a problem. Therefore, it is generally sufficient to merely insure that air bubbles to not accumulate or remain in these positions. Moving the air bubbles to other positions within the ultrasound probe housing will typically facilitate reliable and proper operation of the ultrasound probe.

Preferably, the first air bubble trap is disposed intermediate the ultrasound transducer and the motor. A linkage for transmitting motion from the motor to the transducer thus extends through an opening in the first air trap.

Each air bubble trap preferably comprises a wide end configured to be disposed within the ultrasound probe housing so as to substantially mitigate movement of air bubbles between the air bubble trap and the housing, a tapered body formed to the wide end and configured to extend away from the window of the ultrasound probe, and a narrow end formed upon the tapered body opposite the wide end. Thus, bubbles move more readily through the bubble trap from the wide end thereof to the narrow end thereof than from the narrow end thereof to the wide end thereof.

An optional stand is configured to hold the ultrasound probe housing in a window downward orientation such that actuation of the ultrasound probe results in mechanical vibration thereof which tends to urge air bubbles away from the window and through the air bubble traps.

Thus, a method for removing air bubbles from an ultrasound probe transducer head and motor comprises the steps of orienting the ultrasound probe such that the transducer head thereof is lowermost and actuating the ultrasound probe such that air bubbles disposed within the transducer head move upward through the first air trap away from the transducer head and air bubbles within the motor similarly move upward through the second air trap away from the motor. The air bubbles from the transducer head thus typicallly pass through both traps. Thus, when the ultrasound probe is subsequently oriented such that the transducer head thereof is not lowermost, the air bubbles do not substantially pass back through the first and second air traps toward the transducer head. Thus, according to the methodology of the present invention, the transducer head and motor are substantially isolated from air bubbles and consequently do not suffer the undesirable effects associated therewith. The present invention provides an air bubble transport surface and an accumulation area such that air bubbles move along the air bubble transport surface to the accumulation area wherein they are captured and then utilized for thermal fluid expansion compensation purposes.

Additionally, the present invention eliminates the requirement for bellows-type fluid expansion compensation means by providing a fluid expansion compensation chamber at the opposite end of the housing from the probe head.. Air bubbles trapped by the second air bubble trap accumulate within the fluid expansion compensation chamber. The compressible air bubbles then expand or compress in response to thermal expansion and contraction of the ultrasound transmissive fluid, thus compensating for temperature changes thereof. When the ultrasound probe of the present invention is initially filled with ultrasound transmissive fluid, a small quantity of air is intentionally left within the fluid expansion compensation chamber so as to perform such function.

Such a fluid expansion compensation chamber may be utilized either with or without air bubble traps. Thus, the fluid expansion compensation chamber may be formed within the ultrasound probe housing, within which air or another gas is permanently trapped such that thermal expansion of the ultrasound transmissive fluid results in corresponding compression of the trapped gas.

These, as well as other advantages of the present invention will be more apparent from the following description and drawings. It is understood that changes in the specific structure shown and described may be made within the scope of the claims without departing from the spirit of the invention.

BRIEF DESCRIPTION OF THE DRAWINGS

FIG. 1, is a cross-sectional side view of a first embodiment of an ultrasound probe having two air traps formed therein and being oriented to have its probe head uppermost;

FIG. 2 is a cross-sectional side view of the ultrasound probe of FIG. 1 showing the ultrasound probe having its probe head lowermost and illustrating the flow of air bubbles through the first and second air bubble traps toward the uppermost end thereof;

FIG. 3 is a cross-sectional side view of the ultrasound transducer of FIG. 1 having the probe head thereof oriented uppermost and showing the trapping of air bubbles by the first and second air bubble traps such that air bubbles are prevented from accumulating within the probe head and motor of the ultrasound probe;

FIG. 4 is a perspective view of the first or uppermost air bubble trap of FIG. 1;

FIG. 5 is a perspective view of the spring retainer of FIG. 1;

FIG. 6 is an enlarged fragmentary cross-sectional side view of the uppermost end of the second air bubble trap of FIG. 1 showing the spring retainer disposed therein and abutting the lowermost motor spring;

FIG. 7 is a perspective view of an alternative configuration of ultrasound probe containing a second embodiment of the first air bubble trap of the present invention; and FIG. 8 is a perspective view of the second embodiment of the first air bubble trap.

DETAILED DESCRIPTION OF THE PREFERRED EMBODIMENT

The detailed description set forth below in connection with the appended drawings is intended as a description of the presently preferred embodiments of the invention, and is not intended to represent the only forms in which the present invention may be constructed or utilized. The description sets forth the functions and sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The ultrasound probe with bubble trap of the present invention is illustrated in FIGS. 1 through 8 which depict two presently preferred embodiments of the invention. Referring now to FIGS. 1 and 6, the ultrasound probe generally comprises a housing 10 having an ultrasound transparent window 12 formed therein. The ultrasound window 12 defines a probe head 14 within which an ultrasound transducer 16 is disposed.

In the preferred embodiment of the present invention, the ultrasound transducer 16 is typically mounted to the housing 10 via pivot pin 18 and is attached to a motor 20 via mechanical linkage 22 which facilitates pivoting of the ultrasound transducer 16 about the pivot pins 18. Those skilled in the art will recognize that various other configurations for mounting and moving the ultrasound transducer 16 so as to facilitate oscillating operation thereof are likewise suitable.

The linkage 22 may either be solid as disclosed in further detail in U.S. Pat. No. 4,913,155 issued on Apr. 3, 1990 to Dow et al., and entitled ULTRASONIC TRANSDUCER PROBE ASSEMBLY or may alternatively be flexible, i.e., a cable, as disclosed in further detail in U.S. Pat. No. 4,841,979 issued on Jun. 27, 1989 to Dow et al. and entitled ULTRASONIC PROSTATE PROBE ASSEMBLY, the contents of both of which are hereby incorporated by reference.

An ultrasound transmissive fluid 24 substantially fills the housing 10, including the probe head 14 thereof. Such ultrasound transmissive fluid 24 is required between the ultrasound transistor 16 and the ultrasound transmissive window 12 so as to facilitate radiation of ultrasound energy from the ultrasound transducer 16 into the patient for therapeutic and/or diagnostic purposes.

A first air bubble trap 28 is disposed proximate the ultrasound transducer 16 and a second air bubble trap 30 is disposed proximate the motor 20. The first air bubble trap 28 comprises a wide end 32 which abuts against and seals to an abutting portion 34 of the housing 10 so as to substantially prevent movement of air bubbles between the first air bubble traps 28 and the housing 10. The first air bubble trap further comprises a tapered portion 36 which extends away from the window 12 toward the motor 20 and a narrow end 38 formed upon the tapered body 36 opposite the wide end 32 thereof.

Similarly, the second air bubble trap 30 comprises a wide end 40 which abuts against and seals to the housing 10, preferably utilizing an O-ring 42. Those skilled in the art will recognize that such and O-ring may similarly be utilized with the first air bubble trap 28, if desired. A tapered portion 44 extends away from the motor 20. A narrow end 46 is formed upon the tapered body 44 opposite the wide end 40 thereof.

A smooth surface 29 is formed upon the inside of the first air bubble trap 28 and a similar smooth surface 31 is formed upon the inside of the second air bubble trap 30. The smooth surfaces 29 and 31 of the first 28 and second 30 air bubble traps, respectively, assure that air bubbles moving therein over do not tend to accumulate thereupon but rather travel easily thereover. The smooth surfaces 29 and 31 preferably extend over the wide ends 32 and 40, tapered portions 36 and 44, and the narrow ends 38 and 46 of each air bubble trap 28 and 30.

A fluid expansion compensation chamber 60 is formed about the narrow end 46 of the second air bubble trap 30. Thus, air bubbles passing through the second air bubble trap 30 accumulate within the fluid expansion compensation chamber 60 where they form a function analogous to that of the bellows of contemporary ultrasound probes. That is, the air bubbles contract or expand in volume in response to expansion and contraction of the volume of the ultrasound transmissive fluid, due to temperature changes thereof.

End plug 48 seals the handle end of the ultrasound transducer body 10, admitting wires 50 thereinto to facilitate the communication of electrical power and data signals. A spring 52 extends downwardly from the motor 20 to a spring retainer 54 (best show in FIG. 5) which is disposed within the wide end 40 of the second bubble trap 30. Radially extending peripheral flanges 56 of the spring retainer 54 snap into and are received within annular groove 58 (as best seen in FIG. 6) formed within the wide end 40 of the second air bubble trap 30. The spring 52 is received within annular groove 60 formed within the spring retainer 54.

As shown in FIG. 1, an air bubble 26 has formed within the probe head 14 intermediate the ultrasound transducer 16 and the window 12. The presence of such an air bubble 26 intermediate the ultrasound transducer 16 and the window 12 during the performance of a therapeutic and/or diagnostic procedure is undesirable since it interferes with the proper operation of the ultrasound transducer.

Referring now to FIGS. 2 and 3, operation of the first 28 and second 30 air bubble traps to remove air bubbles from the probe head 14 and motor 20 and to maintain isolation of the air bubbles from the probe head 14 and the motor 20 is shown. With particular reference FIG. 2, orienting the ultrasound probe with the probe head 14 lowermost causes air bubbles disposed within the probe head 14 and the motor 20 to rise, passing through the first 28 and/or second 30 air bubble traps. Typically, air bubbles disposed within the probe head 14 will rise upwardly through both the first 28 and second 30 air bubble traps to become positioned within the fluid expansion compensation chamber 60. In the fluid expansion compensation chamber 60, the air bubbles function in a desirable manner to compensate for thermal expansion of the ultrasound transmitting fluid within the housing 10, as discussed above.

As mentioned above, the inside surface 29 of the first 28 and the inside surface 31 of the second 30 air bubble traps are smooth, preferably polished, such that air bubbles do not tend to cling thereto, but rather easily move therealong, when the probe head 14 is held lowermost. Thus, movement of air bubbles in the desired direction, i.e., away from the probe head, is facilitated.

For example, an air bubble disposed within the probe head 14 would travel upward and contact the smooth surface 29 of the first air bubble trap 28 and then move therealong to the aperture 33 formed at the narrow end 38 of the first air bubble trap 28. The air bubble would continue to rise and pass through the first aperture 19 of the motor, through the motor 20 itself, and out through the second aperture 21 of the motor 20. From there the air bubble would rise into the second air bubble trap 30, typically contacting the smooth surface 31 thereof and exiting through the aperture 35 formed in the narrow end 46 thereof. Air bubbles 62 thus accumulate within the fluid expansion compensation chamber 60.

With particular reference to FIG. 3, upon reorienting the ultrasound probe such that the probe head 14 thereof is no longer lowermost, as would occur during use, handling, and/or storage thereof, the air bubbles 62 which have become trapped within the fluid expansion compensation chamber 60 typically do not re-enter the small diameter aperture 35 of the narrow end 46 of the second air trap 30, rather the air bubbles 62 rise and become lodged about the outer surface of the wide end 41 of the second air bubble trap 30. Because of its small diameter, it is unlikely that the air bubbles will re-enter the aperture 35 of the second air bubble trap 30.

Any air bubbles 64 which either did not pass through the second air bubble trap 30 when the probe head 14 was lowermost or which did manage to travel backwards through the second air bubble trap 30 after the probe head 14 was no longer held lowermost, would most likely become trapped by the first air bubble trap 28 and thus become lodged proximate the wide end 32 thereof. As with the second air bubble trap 30, the aperture 33 of the first air bubble trap is of a small diameter such that any air bubbles rising through the housing 10 are not likely to enter the narrow end 38 of the first air bubble trap 28, but rather are more likely to become trapped proximate the wide end 32 thereof.

Thus, air bubbles may be cleared from the probe head 14 by merely positioning the ultrasound probe in a probe head 14 downward orientation. The ultrasound probe is preferably actuated such that the vibration thereof caused by the motor 20 aids in causing the bubbles to travel upward through the first 28 and second 30 air traps. Such vibration loosens the bubbles from any surfaces that they may cling to and tends to prevent adhering of the air bubbles to surfaces which they contact as they rise through the housing 10.

Optionally, the ultrasound probe may be oriented probe head 14 down and placed in a stand. The ultrasound probe could then be activated and let sit for a period of time to allow the air bubbles to travel upward and become trapped. Those skilled in the art will recognize that various configurations of such stands are suitable.

Additionally, normal usage of the ultrasound probe will typically result in any air bubbles disposed within the housing 10 ultimately being trapped within the fluid expansion compensation chamber 60, since many of the common diagnostic and therapeutic procedures are performed with the probe head 14 lowermost. Thus, the ultrasound probe is frequently oriented in a manner which is conducive to trapping of the air bubbles away from the probe head and motor thereof during normal use. Actuation of the ultrasound probe motor, inherent to the ultrasound scanning process, further facilitates trapping of air bubbles. Thus, specific procedures, as described above, to eliminate air bubbles within the probe head 14 and motor 20, are typically not required. Normal use of the ultrasound probe is generally sufficient to trap the air bubbles away from the window 12 and motor 20.

Referring now to FIG. 4, the first air bubble trap 28 is illustrated. Both the first 28 and second 30 air bubble traps are preferably configured as funnels. However, those skilled in the art will recognize that various other shapes may similarly be utilized so as to conform to the different designs of ultrasound probes.

Referring now to FIG. 5, the spring retainer 54 comprises an annulus 55 having an annular groove 60 formed therein for receiving the spring 52 and has flanges 56 extending radially therefrom. A central opening 61 is provided in the spring retainer 54 so as to facilitate the movement of air therethrough. Air bubbles also may move through the spaces 57 formed intermediate adjacent flange 56. The flanges 56 attach the spring retainer 54 to the wide end 40 of the second air bubble trap 30 via the annular groove 58 formed therein, as discussed above.

Referring now to FIGS. 7 and 8, a second embodiment of the ultrasound probe with bubble trap invention of the present invention is illustrated. In the second embodiment of the present invention, the probe head 14a is configured to have an elongate shape so as to facilitate long or wide angle sweeps of the ultrasound sensor as disclosed U.S. Ser. No. 07/980,583, filed on Nov. 23, 1992 and entitled ULTRASOUND PERIPHERAL VASCULAR PROBE ASSEMBLY, the contents of which are hereby incorporated by reference.

To accommodate the configuration of the elongate probe head 14a, the first air bubble trap 28a is of a similar elongate configuration, preferably generally rectangular. Thus, the wide end 32a of the first air bubble trap 28a is configured to be generally rectangular in configuration so as to properly fit within and seal to the probe head 14a. Those skilled in the art will recognize that various other configurations of the first and second air bubble traps are likewise suitable for conforming to and sealing with various other components and configurations of various ultrasound probes.

Thus, an air bubble transport surface comprising first and second air bubble traps facilitates movement of air bubbles away from portions of the ultrasound probe where the presence of such air bubbles is not desired. The air bubbles are moved to an accumulation area wherein the air bubbles do not undesirably affect operation of the ultrasound probe and indeed function desirably as a thermal fluid expansion compensator.

It is understood that the exemplary ultrasound probe with bubble trap described herein and shown in the drawings represents only a presently preferred embodiment of the invention. Indeed, various modifications and additions may be made to such embodiments without departing from the spirit and scope of the invention. For example, the air bubble traps need not be generally funnel-like in configuration, but rather any configuration wherein one end thereof has a much smaller cross-sectional area than the other end thereof is suitable. Indeed, more than a single aperture may be formed within either end of the air bubble trap, as desired. As such, the air bubble traps of the present invention may be utilized in a wide variety of different ultrasound probe designs and configurations. Thus, these and other modifications and additions may be obvious to those skilled in the art and may be implemented to adapt the present invention for use in a variety of different applications.

What is claimed is:

1. An ultrasound probe comprising:
   a) a housing;
   b) an ultrasound transmissive window formed to said housing;
   c) a motor disposed within said housing;
   d) a first air bubble trap disposed proximate said window;
   e) a second air bubble trap disposed proximate said motor such that said motor is disposed intermediate said first and second air bubble traps;
   f) wherein said first air bubble trap isolates said window from air bubbles and said second air bubble trap isolates said motor from air bubbles; and
   g) an accumulation area to which said air bubble traps moves the air bubbles, said accumulation area being an area where air bubbles do not have an undesirable effect upon operation of the ultrasound probe.

2. The ultrasonic probe of claim 1 wherein said accumulation area is of sufficient size such that the housing does not require a vent for extracting the air bubbles from the housing.

3. The ultrasound probe as recited in claim 1 wherein said accumulation area and the air bubbles disposed therein define a fluid expansion compensation chamber.

4. The ultrasound probe as recited in claim 1 wherein said first and second air bubble traps comprise:
   a) the first air bubble trap configured as a funnel having a narrow end thereof extending away from said window, said first air bubble trap attached at a periphery of a wide end thereof to said housing in a manner so as to prevent air bubble movement intermediate said first air trap and said housing; and
   b) the second air bubble trap configured as a funnel having a narrow end thereof extending away from said motor, said second air bubble trap attached to a periphery of a wide end thereof to said housing in a manner so as to prevent air bubble movement intermediate said second air trap and said housing.

5. The ultrasound probe as recited in claim 1 further comprising a stand configured to hold said housing in a window oriented downward such that actuating of said ultrasound probe results in mechanical vibration thereof which tends to urge air bubbles away from said window and through said air trap(s).

* * * * *